United States Patent [19]

Schwan

[11] 4,001,245

[45] Jan. 4, 1977

[54] 2-[2-(PIPERIDINO)ETHYL]-10,10A-DIHYDRO-1H,5H-IMIDAZO[1,5-b]ISOQUINOLIN-1,3(2H)-DIONE

[75] Inventor: Thomas J. Schwan, Norwich, N.Y.

[73] Assignee: Morton-Norwich Products, Inc., Norwich, N.Y.

[22] Filed: Dec. 2, 1975

[21] Appl. No.: 636,913

[52] U.S. Cl. .......................... 260/287 CF; 424/258
[51] Int. Cl.$^2$ ...................................... C07D 471/14
[58] Field of Search ............................. 260/287 CF

[56] References Cited

OTHER PUBLICATIONS

March, "Advanced Organic Chemistry" 1968, p. 340.

Primary Examiner—Donald G. Daus
Assistant Examiner—David E. Wheeler
Attorney, Agent, or Firm—Anthony J. Franze

[57] ABSTRACT

The title compound possesses pharmacological activity as an anti-inflammatory agent.

1 Claim, No Drawings

2-[2-(PIPERIDINO)ETHYL]-10,10a-DIHYDRO-1H,5H-IMIDAZO[1,5-b]ISOQUINOLIN-1,3(2H)-DIONE

This invention relates to chemical compounds. In particular it is concerned with a compound of the formula.

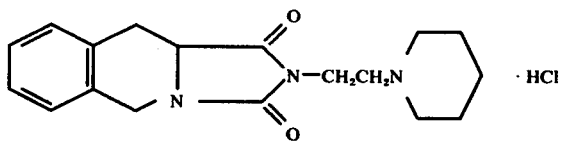

This compound possesses pharmacological activity. It is particularly effective as an anti-inflammatory agent as evidenced by its ability to inhibit edema induced in rats by the administration of carrageenin. Thus, when administered at a dose of 300 mg/kg suspended in a vehicle such as aqueous methyl cellulose per os to rats receiving carrageenin, edema associated with that substance is inhibited [Winter et. al., P.S.E.B.M 14,544 (1964)].

In order that this invention be readily available to and understood by those skilled in the art, the following examples are illustrated:

A. 10,10a-Dihydro-1H,5H-imidazo[1,5-b]isoquinolin-1,3(2H)-dione

To a suspension of 53.1 g (0.30 mole) of 1,2,3.4-tetrahydroisoquinoline-3-carboxylic acid in 1000 ml glacial acetic acid was added quickly a solution of 48.6 g (0.60 mole) of potassium cyanate in 150 ml water. The mixture was stirred and heated on a steam bath at 90°–95° for 90 min and all solids dissolved. 3N hydrochloric acid (2400 ml) was added and the resulting solution was stirred and refluxed for 20 hr. The solution was filtered while hot through a coarse sintered glass funnel to remove mechanical impurities and the filtrate was stored in the refrigerator for 18 hrs to deposit 44 g of the crude product. Recrystallization from 1400 ml alcohol gave 29.9 g (49%) of the cyclized material, m.p. 225°–231°. Further recrystallization from alcohol gave the analytical sample, m.p. 227°–230°.

Anal. Calcd. for $C_{11}H_{10}N_2O_2$: C, 65.33; H, 4.98; N, 13.86. Found: C, 65.41; H, 4.80; N, 13.90.

B. 2-[2-(Piperidino)ethyl]-10,10a-dihydro-1H,5H-imidazo[1,5-b]isoquinolin-1,3(2H)-dione Hydrochloride A mixture of 26.5 g (0.131 mole) of A, 48.2 g (0.262 mole) of N-(2-chloroethyl)piperidine·HCl; 54.2 g (0.393 mole) potassium carbonate, and 19.7 g (0.131) sodium iodide in 900 ml dimethyl sulfoxide was stirred at 50°–55° for 48 hr. An additional 24.1 g (0.131 mole) of N-(2-chloroethyl)-piperidine hydrochloride was added to the mixture and stirring was continued at 50°–55° for an additional 24 hr. The mixture was cooled and poured into 2.0 l cold water. The mixture was extracted with 4×400 ml chloroform and the combined extracts were washed with 2×800 ml water, dried and concentrated to dryness. The oil was boiled with 180 ml of ethanol and the suspension stored in a refrigerator for 2 weeks. Filtration gave 9.0 g unreacted A.

To the filtrate was added 40 ml methanol saturated with hydrogen chloride. The resulting solid was recrystallized from 125 ml ethanol to yield, after drying at 100° for 4 hr, 7.9 g (26% based on consumed A) of the product, m.p. 204°–207°. The analytical sample, m.p 237°–239°, was obtained by recrystallization from ethanol.

Anal. Calcd. for $C_{18}H_{23}N_3O_2·HCl$: C, 61.79; H, 6.91; N, 12.01. Found: C, 61.78; H, 7.02; N, 11.86.

What is claimed is:
1. A compound of the formula:

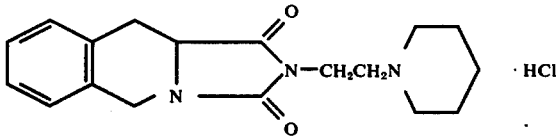

* * * * *